United States Patent [19]

Jenkins, Jr.

[11] 4,124,600

[45] Nov. 7, 1978

[54] PREPARATION OF TETRAHYDROFURAN

[75] Inventor: Colie L. Jenkins, Jr., Memphis, Tenn.

[73] Assignee: E. I. Du Pont de Nemours and Company, Wilmington, Del.

[21] Appl. No.: 581,566

[22] Filed: May 28, 1975

[51] Int. Cl.$^2$ ............................................. C07D 307/08
[52] U.S. Cl. ................................................ 260/346.11
[58] Field of Search ................................. 260/346.1 R

[56] References Cited

U.S. PATENT DOCUMENTS

| | | | |
|---|---|---|---|
| 2,251,835 | 8/1941 | Reppe et al. | 260/346.1 R |
| 2,251,895 | 8/1941 | Reppe et al. | 260/346.1 R |
| 3,165,536 | 1/1965 | Strohmeyer | 260/346.1 R |
| 3,346,336 | 10/1967 | Hayes | 252/463 |
| 4,010,171 | 3/1977 | Smith | 260/346.1 R |
| 4,011,244 | 3/1977 | Smith | 260/346.1 R |

FOREIGN PATENT DOCUMENTS

| | | | |
|---|---|---|---|
| 547,798 | 10/1957 | Canada | 260/346.1 R |
| 2,062,950 | 7/1971 | Fed. Rep. of Germany | 260/346.1 R |
| 506,674 | 6/1939 | United Kingdom | 260/346.1 R |
| 1,170,222 | 11/1969 | United Kingdom | 260/346.1 R |

OTHER PUBLICATIONS

Zhdanov et al., Chem. Abstr. vol. 45 (1951) 8863i.

Primary Examiner—Henry R. Jiles
Assistant Examiner—Bernard Dentz

[57] ABSTRACT

Tetrahydrofuran is prepared by the vapor phase reaction of a compound selected from 1,4-butanediol, monoesters of 1,4-butanediol, diesters of 1,4-butanediol and mixtures thereof in the presence of water and an acid catalyst wherein the catalyst is selected from phosphoric acid on a suitable support and eta alumina at a temperature of from about 200° to about 325° C followed by the recovery of the tetrahydrofuran by distillation.

12 Claims, No Drawings

PREPARATION OF TETRAHYDROFURAN

BACKGROUND OF THE INVENTION

1. Field of the Invention

This invention relates to the preparation of tetrahydrofuran. More specifically this invention relates to the preparation of tetrahydrofuran from butanediol and mono- and diesters thereof.

2. Description of the Prior Art

A process for the preparation of tetrahydrofuran by the catalytic dehydration of 1,4-butanediol is described in U.S. Pat. No. 2,251,835. However this process, which is conducted so that there is always a substantial amount of the reaction mixture in the liquid phase, suffers because the acid catalyst would be washed off from a support thereby shortening catalyst life unless the catalyst is constantly replaced and because a waste acid stream results.

Tetrahydrofuran can also be prepared by the catalytic oxidation of olefins to produce carboxylic esters which are then hydroformylated, hydrogenated and hydrolyzed. For example, the oxidation of propylene to allyl acetate followed by hydroformylation to produce 4-acetoxybutan-1-ol or oxidation of butenes or butadiene to produce 1,4-diacetoxy butyl derivates which can be hydrogenated to 1,4-diacetoxybutane. However, when the carboxylic esters such as, for example, the mono- or diacetate derivatives of 1,4-butanediol are subjected to strong mineral acids such as sulfuric acid for the hydrolysis/cyclization, the tetrahydrofuran produced is accompanied by a significant amount of high boiling materials and tars. Additionally in order to obtain high yields of tetrahydrofuran, it is necessary to continuously remove the acetic acid formed or dilute the system with water. German patent application No. 2,062,950 discloses the removal of acetic acid by distillation. U.S. Pat. No. 3,586,716 discloses the removal of acetic acid by use of a low boiling ether. However, the removal of carboxylic acid by distillation or dilution with large excesses of water are required to achieve high conversions and yields to tetrahydrofuran which results in low space time throughputs. Additionally, the use of a low boiling ether to extract carboxylic acids makes the purification of the tetrahydrofuran product more difficult. The strong mineral acid catalysts used in the formation of tetrahydrofuran results in the production of a waste stream, referred to herein as waste acid streams, which must be neutralized or incinerated and thereby raises a waste disposal problem.

SUMMARY OF THE INVENTION

Now it has been discovered that tetrahydrofuran can be prepared by reacting in the vapor phase a compound selected from 1,4-butanediol, carboxylic ester derivatives of 1,4-butanediol and mixtures thereof in the presence of water or steam and an acid catalyst selected from phosphoric acid on a suitable support structure and eta alumina and recovering tetrahydrofuran.

Thus, according to the invention, tetrahydrofuran can be prepared in high yields, conversions and reaction rates without creating waste acid streams by a process comprising reacting a compound selected from 1,4-butanediol, monoesters of 1,4-butanediol, diesters of 1,4-butanediol and mixtures thereof in the vapor phase in the presence of water, preferably 1 to 10 moles of water per molar equivalent of the reacting compound and an acid catalyst wherein the catalyst is selected from phosphoric acid on a suitable support and eta alumina at a temperature of from about 200° to about 325° C to form tetrahydrofuran in a reaction mixture and recovering the tetrahydrofuran from the reaction mixture.

When the process of the invention utilizes either cis or trans 1,4-butenediol or its mono- or diester, 2,5-dihydrofuran is produced. Thus, other furan-type derivatives can be prepared by the process of the invention than tetrahydrofuran. Alkyl substituted tetrahydrofuran can also be prepared according to the present invention. For example, when 2-methyl-1,4-butanediol or its mono- or diesters are used the product is 3-methyl-tetrahydrofuran.

The monoester and diester of 1,4-butanediol may be represented by the formula

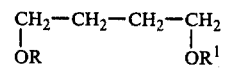

where R and $R^1$ are selected from hydrogen and $R^2$-C=O where $R^2$ is hydrogen or alkyl radical from 1 to 5 carbon atoms, preferably less than 3.

Representative monoesters include 4-propoxybutan-1-ol, 4-acetoxybutan-1-ol, 4-formoxybutan-1-ol, 4-acetoxy-3-methylbutan-1-ol, 4-acetoxy-2-methylbutan-1-ol, 4-acetoxy-2-buten-1-ol, and the like.

Representative diesters include 1,4-diacetoxy-butane, 1,4-diacetoxy-2-methylbutane, 1,4-diacetoxy-2-butene, 1,4-diacetoxy-2,2-dimethylbutane, 1,4-diacetoxy-2,3-dimethylbutane, 1,4-diformoxybutane, 1,4-dipropoxybutane and the like.

Thus, the process of the present invention does not utilize a strong mineral acid in the liquid phase to catalyze the ring closure of the starting compounds of the present invention so as to create or involve a waste acid stream in the final reaction mixture. The phosphoric acid is not present in the product stream to the extent necessary to have a waste acid stream in the final reaction mixture or product that would require neutralization. The catalytic amount of 10 to 50% phosphoric acid and 90 to 50% support material is not sufficient to constitute any acid stream that would require neutralization before disposal.

The present invention involves the preparation of acetic acid as a byproduct that can be recovered and used in the preparation of the starting ester compounds of the present invention.

The starting compounds of the present invention may be prepared according to methods well known in the art. For example, 1,4-butanediol may be prepared according to the methods described in British Pat. No. 1,242,358. The carboxylic esters of 1,4-butanediol may be prepared by the oxidation of propylene to allyl acetate followed by hydroformylation or by the oxidation of butene or butadiene. German Offenlegung No. 2,200,124 describes such preparations.

The acid catalyst of the present invention is selected from phosphoric acid on a suitable support and eta alumina. An acid catalyst of the present invention is phosphoric acid. Another acid catalyst of the present invention is eta alumina. The phosphoric acid catalysts of the present invention is applied to supports of inert or catalytically active material such as, for example, silica, natural and synthetic silicates, silica-alumina, alumina, silica gel, active carbon, aluminum oxide spinels, pumice, kieselguhr, diatomaceous earth, clay, titanium dioxide or the like. By aluminum oxide as a supporting material is not meant eta aluminum which is an active catalyst of the present invention.

Eta alumina is a specific form of aluminum oxide which can be prepared from Bayrite (aluminum hydroxide) by special conditions of pressure, humidity, and heating rate. For example, heating Bayrite of a particle size less than 10 microns in a dry atmosphere of air, at atmospheric pressure, and at a slow heating rate (less than 1° C per minute up to 300° to 500° C) produces eta alumina. If one heats the sample too rapidly or uses large particles in moist air, the gamma form of alumina is formed. Eta alumina can be distinguished from the many other forms of alumina by examination of its X-ray diffraction pattern. Eta alumina is a cubic (spinel) structure with a lattice constant of Ao = 7.90 A. A comprehensive study of the various forms of alumina can be found in "Oxides and Hydroxides of Aluminum", Aluminum Company of America, Technical Paper No. 19 (1972) by K. Wafers and G. M. Bell.

The phosphoric acid catalyst of this invention with the support material may constitute from 5 to 50% preferably 10% by weight phosphoric acid and 95 to 50% by weight support material. The phosphoric acid solution mixed with the support material to attain a phosphoric acid impregnated support material may vary from 5 to 90% phosphoric acid.

A catalytic amount of catalyst is required. The catalytic amount can vary broadly. The amount of catalyst relative to the reactants will be very large because of the vapor phase reaction and the solid catalyst as such or the catalyst impregnated support. Generally the amount of catalyst to reactant varies widely over a range of conditions of temperature, pressure and feed rate. Thus, the amount depends on the residence time which may be as low as 1 second and as high as 1 minute, preferably 2 to 6 seconds. Residence time is defined as the volume of the catalyst divided by the feed rate. It is preferred that the catalytic amount range from that amount that under the conditions of the process of the invention will yield a STY of from 150 to 500.

The process of the invention can be carried out at temperatures of from about 200° to about 325° C, preferably from about 225° to about 300° C. At temperatures above 325° C formation of 1,3-butadiene reaches an undesirable level. At temperatures below 200° C the rate of reaction is too low resulting in low conversions, e.g., see Example 4.

The process of the invention can be carried out in an atmosphere containing oxygen provided that it is outside the explosive range for products and reactants. However, an inert atmosphere, for example, nitrogen is preferred. Subject therefore to any explosive range, the process of this invention may be carried out at a pressure of from about 100 mm Hg to 100 psig, preferably at atmospheric pressure. The process of the present invention requires a pressure that will maintain a vapor phase reaction of the reactants at the temperature desired.

The process of the invention permits longer catalyst life than heretofore possible.

The term STY used herein refers to the space, time, yield which is the weight of tetrahydrofuran (THF) per liter of catalyst per hour.

The process of this invention may be carried out batchwise or continuously although continuous operation is preferred.

The following examples serve to further illustrate the invention and are not intended to restrict the scope of the invention to the examples that follow. All percentages are by weight unless otherwise indicated.

EXAMPLE 1

A liquid feed of 0.0886 mole of 1,4-diacetoxybutane, 0.043 mole 4-acetoxybutan-1-ol and 0.004 mole 1,4-butanediol was pumped into a vaporizing chamber from a syringe pump at the rate of 0.5 cc/min. The same pump was used to deliver water from a separate syringe at 0.5 cc/min. A gas stream of nitrogen was also fed to the vaporizing chamber at the rate of 300 cc/min. The exit gas from the vaporizing chamber was then passed through a tubular reactor which contained 50 cc alumina which had been impregnated with 10% phosphoric acid. The reactor temperature was maintained by an electrically heated furnace, which in this case was 250° C. The exit from the reactor was then passed through an ice bath to condense the products. The products were analyzed by gas chromatography except for acetic acid which was analyzed by titration with 0.1 N sodium hydroxide solution. Analysis of the condensate showed the 1,4-butanediol and 4-acetoxybutan-1-ol to be completely reacted and 0.0053 mole of 1,4-diacetoxybutane remaining. The acetic acid was found to be 0.1897 mole or 90% of theoretical and the tetrahydrofuran was 0.110 mole or 81% of theoretical. The off gas from the condenser was shown to contain tetrahydrofuran amounting to approximately 0.020 moles or 14% of theoretical and butadiene to the extent of 2 to 3% yield. The space, time, yield, hereinafter referred to as STY, of tetrahydrofuran was 280 grams per liter of catalyst per hour.

EXAMPLES 2–4

The procedure of Example 1 was followed using the same catalyst charged and the same amounts of reactants. The data obtained is summarized in Table I.

TABLE I

| Example | $N_2$ Flow cc/min | Temp. °C | Pressure | Overall[a] % Conversion to THF |
|---|---|---|---|---|
| 2 | 175 | 225 | Atmospheric | 68 |
| 3 | 300 | 200 | " | 60 |
| 4 | 300 | 175 | " | 31 |

[a]In all cases the 1,4-butanediol was completely converted.

EXAMPLE 5

Following the procedure of Example 1, 0.224 mole of 1,4-butanediol and 1.11 moles of water were reacted at 250° C with a nitrogen flow rate of 175 cc/min. This resulted in a complete conversion of the 1,4-butanediol and produced 0.209 moles of tetrahydrofuran. The STY of tetrahydrofuran was 452 grams per liter of catalyst per hour.

EXAMPLE 6

The reaction described in Example 5 was followed except that the temperature was 200° C. A complete conversion of the 1,4-butanediol resulted and 0.214 mole of tetrahydrofuran was produced. The STY of tetrahydrofuran was 462 grams per liter of catalyst per hour.

The tetrahydrofuran and acetic acid produced in Examples 2 through 6 was combined and distilled through a 2-foot Oldershaw column. The low boiling fraction, i.e., 64° to 75° C was an azeotrope of tetrahydrofuran and water which was 94% tetrahydrofuran.

The purification of this low boiling fraction can be easily done by known techniques.

A higher boiling fraction, i.e., 75° to 118° C was next recovered and found to be an azeotrope of acetic acid and water. The acetic acid may be purified by known distillation techniques. However, the acetic acid and water azeotrope may be used in the metal catalyzed oxidation process which converts olefins to acetate derivatives thereof. The distillation bottoms after recovery of tetrahydrofuran and acetic acid may be recycled to the reactor system and a further conversion increase obtained.

EXAMPLES 7–9

The procedure of Example 1 was followed except that the feed was 0.18 mole 4-acetoxybutan-1-ol and 0.107 mole 1,4-diacetoxybutane. The temperature was 225° C and the nitrogen flow rate 200 cc/min. The amount of water was varied by varying the syringe feed of this pump so that the water was fed over the same time span as the acetate feed. The data and results are summarized in Table II.

TABLE II

| Example | Moles of Water Fed | % Conversion | STY of THF g/l × hr |
|---------|-------------------|--------------|---------------------|
| 7 | 1.11 | 86.4 | 270 |
| 8 | 0.835 | 86.9 | 213 |
| 9 | 0.275 | 81.7 | 223 |

EXAMPLES 10–12

The procedure of Example 1 was followed except that the feed was 0.1136 mole 1,4-diacetoxybutane, and 1.11 mole of water. The nitrogen flow rate was 175 cc/min. In these cases the catalyst was 50 cc of eta alumina. The data obtained is summarized in Table III.

TABLE III

| Example | Temperature | % Conversion | STY of THF g/l × hr |
|---------|-------------|--------------|---------------------|
| 10 | 250 | 98 | 240 |
| 11 | 225 | 90 | 228 |
| 12 | 225 | 94 | 230 |

EXAMPLE 13

The procedure of Example 1 was followed except that a feed of 0.0103 mole of 2-methyl-4-acetoxy-1-butanol, 0.103 mole of 2-methyl-1,4-diacetoxybutane, and 0.555 mole of water were reacted at 225° C over 50 cc of 10% phosphoric acid on alumina for 40 minutes. The nitrogen flow rate was 150 cc/min. This resulted in an 80% conversion and a space, time, yield (STY) of 3-methyl tetrahydrofuran of 277 grams per liter of catalyst per hour.

EXAMPLE 14

The procedure of Example 1 was followed except that a feed of 0.147 mole of 2-methyl-1,4-butanediol and 0.284 mole of water were reacted at 225° C and a nitrogen flow of 125 cc/min. This resulted in complete conversion of a STY of 3-methyl tetrahydrofuran of 368 grams per liter of catalyst per hour.

EXAMPLE 15

A liquid phase hydrolysis/cyclization reaction was conducted using 0.0163 mole 4-acetoxybutan-1-ol and 0.0897 mole 1,4-diacetoxybutane with 1.11 moles of water and 3.7 g of sulfuric acid (8.3% of mixture) in a 100 cc reactor to which a distillation head was attached. The takeoff to reflux ratio was 1:1. The distillate was analyzed by gas chromatography to determine the amount of tetrahydrofuran produced and the amount of acetic acid was determined by titration with a standard sodium hydroxide solution. A very slow reaction rate resulted even though the tetrahydrofuran was continuously removed from the reaction mixture. The data obtained is summarized in Table IV. The average STY for THF in this example was 5.8 g/1/hr.

TABLE IV

| Reaction Temp. °C | Total Lapsed Time (hr.) | Distillate Temp. °C | Cumulative % Yields in Distillate | |
|---|---|---|---|---|
| | | | THF | HOAc |
| 102 | 7 | 60–80 | 43.5 | 1.2 |
| 102 | 10 | 80 | 51.0 | 4.4 |
| 105 | 18 | 80 | 67.5 | 15.0 |
| 107 | 22 | 80–101 | 70.1 | 23.4 |
| 115 | 24 | 101–104 | 71.0 | 44.3 |
| 158 | 25 | 104–105 | 71.5 | 79.8 |
| 180 | 25.5 | 105 110 | 71.5 | 86.1 |

The residue was charred and tarry.

The product of this invention, tetrahydrofuran, is useful as a solvent, and as a fiber intermediate.

While certain representative embodiments and details have been shown for the purpose of illustrating the invention, it will be apparent to those skilled in the art that various changes and modifications may be made therein without departing from the spirit and scope of the invention.

What is claimed is:

1. A process for the preparation of tetrahydrofuran comprising contacting the monoester of 1,4-butanediol of the formula

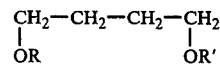

where R and R' are selected from hydrogen and

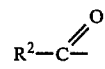

and at least one of R or R' is

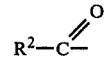

where $R^2$ is hydrogen or an alkyl radical of 1 to 5 carbon atoms or mixtures of said monoester with a diester of the above formula in the vapor phase in the presence of water or steam with a catalytic amount of a catalyst selected from phosphoric acid on a support material and eta alumina at a temperature of from about 200° to about 325° C, wherein the monoester or said mixtures are contacted with the catalyst from 1 second to 1 minute, and recovering the tetrahydrofuran from the reaction mixture.

2. The process of claim 1 wherein the catalyst is phosphoric acid on a support material.

3. The process of claim 1 wherein the catalyst is eta alumina.

4. The process of claim 1 wherein R is hydrogen and $R_2$ is an alkyl radical of 1 to 5 carbon atoms.

5. The process of claim 4 wherein the catalyst is phorphoric acid on a support material.

6. The process of claim 4 wherein the acid catalyst is eta alumina.

7. The process of claim 1 wherein mixtures of the monoester and the diester are contacted.

8. The process of claim 7 wherein the catalyst is eta alumina.

9. The process of claim 7 wherein the catalyst is phosphoric acid on a support material.

10. The process of claim 1 wherein the monoester is contacted.

11. The process of claim 10 wherein the catalyst is eta alumina.

12. The process of claim 11 wherein the catalyst is phosphoric acid on a support material.